US006492575B1

(12) United States Patent
Wagner et al.

(10) Patent No.: US 6,492,575 B1
(45) Date of Patent: *Dec. 10, 2002

(54) METHOD FOR DEVELOPING TRANSGENIC MICE

(75) Inventors: Erwin Wagner, Vienna (AT); Zhao-Qi Wang, Lyon (FR)

(73) Assignee: Boehringer Ingelheim International GmbH, Ingelheim am Rhein (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,406

(22) PCT Filed: Aug. 9, 1997

(86) PCT No.: PCT/EP97/04352

§ 371 (c)(1),
(2), (4) Date: Dec. 28, 1999

(87) PCT Pub. No.: WO98/06834

PCT Pub. Date: Feb. 19, 1998

(30) Foreign Application Priority Data

Aug. 13, 1996 (DE) .......................................... 196 32 532

(51) Int. Cl.[7] ....................... A01K 67/027; C12N 15/00; C12N 15/63; C12N 15/85; C12N 15/87
(52) U.S. Cl. ............................... 800/25; 800/18; 800/21; 800/8; 800/13; 435/455
(58) Field of Search .......................... 435/288.3, 305.1, 435/455; 800/14, 7, 25, 18, 8, 13, 21

(56) References Cited

U.S. PATENT DOCUMENTS 5,523,226 A 6/1996 Wheeler ................... 435/240.2
5,942,435 A 8/1999 Wheeler ..................... 435/325
6,331,406 B1 12/2001 Gearhart et al. ........... 435/7.21

OTHER PUBLICATIONS

Chen, L.R., et al., "Establishment of Pluripotent Cell Lines from Porcine Preimplantation Embryos," *Theriogen.* 52:195–212 (1999).
Shim, H., et al., "Isolation of Pluripotent Stem Cells from Cultured Porcine Primordial Germ Cells," *Biol. Reprod.* 57:1089–1095 (Nov. 1997, but publicly available at least as of Oct. 28, 1997).
Wheeler, M.B., and Walters, E.M., "Transgenic Technology and Applications in Swine," *Theriogen.* 56:1345–1369 (2001).
Beardsley, T., "Stem Cells Come of Age," *Sci. Am. (Jul. issue)*, pp. 30–31, Scientific American, Inc., New York, NY (1999).
Call, L.M., et al., "A Cre–lox recombination system for the targeted integration of circular yeast artificial chromosomes into embryonic stem cells," *Human Molec. Genet.* 9:1745–1751, Oxford University Press, Oxford, UK (2000).

Edwards, B.E., et al., "The human pluripotent stem cell: impact on medicine and society," *Fertil. Steril.* 74:1–7, Elsevier Science Inc., New York, NY (2000).
Marshall, V.S., et al., "Isolation and Maintenance of Primate Embryonic Stem Cells," *Meth. Molec. Biol.* 158, 11–18, Humana Press, Inc., Totowa, NJ (2001).
Pirity, M., et al., "Embryonic Stem Cells, Creating Transgenic Animals," *Meth. Cell Biol.* 57:279–293, Academic Press, Inc., San Diego, CA (1998).
Shamblott, M.J., et al., "Derivation of pluripotent stem cells from cultured human primordial germ cells," *Proc. Natl. Acad. Sci. USA* 95:13726–13731, The National Academy of Sciences of the U.S.A., Washington, DC (Nov. 1998).
Shamblott, M.J., et al., "Human embryonic germ cell derivatives express a broad range of developmentally distinct markers and proliferate extensively in vitro," *Proc. Natl. Acad. Sci. USA* 98:113–118, The National Academy of Sciences of the U.S.A., Washington, DC (2001).
Stice, S.L., et al., "Pluripotent Bovine Embryonic Cell Lines Direct Embryonic Development Following Nuclear Transfer," *Biol. Reprod.* 54:100–110, Society for the Study of Reproduction, Madison, WI (1996).
Strelchenko, N., "Bovine Pluripotent Stem Cells," *Theriogenology* 45:131–140, Elsevier Science Inc., New York, NY (1996).
Thomson, J.A., et al., "Embryonic Stem Cell Lines Derived from Human Blastocysts," *Science* 282:1145–1147, American Assn. for the Advancement of Science, Washington, DC (Nov. 1998).
Thomson, J.A., and Odorico, J.S., "Human embryonic stem cell and embryonic germ cell lines," *Trends Biotechnol.* 18: 53–57, Elsevier Science Inc., New York, NY (2000).
Wheeler, M.B., "Development and Validation of Swine Embryonic Stem Cells: a Review," *Reprod. Fertil. Dev.* 6:563–568, CSIRO Publishing, Melbourne, Australia (1994).
U.S. Department of Health and Human Services/NIH, "National Institutes of Health Guidelines for Research Using Human Pluripotent Stem Cells," 19 Biotechnol. Law Rep. 875–880, Mary Ann Liebert, Inc., Larchmont, NY (2000).
Beddington, R.S.P. and Robertson, E.J., "An assessment of the developmental potential of embryonic stem cells in the midgestation mouse embryo," *Development* 105:733–737 (1989).
Bradley, A., in *Teratocarcinomas and Embryonic Stem Cells: a Practical Approach*, Robertson, E. J., ed., IRL Press, Oxford, pp. 113–151 (1987).

(List continued on next page.)

Primary Examiner—Scott D. Priebe
Assistant Examiner—Peter Paras, Jr.
(74) Attorney, Agent, or Firm—Sterne Kessler Goldstein & Fox P.L.L.C.

(57) ABSTRACT

Process for producing mammals with defined genetic properties, particularly transgenic mammals. Animals which are derived completely from ES cells are obtained by injecting totipotent cells (embryonic stem cells or embryonic germ cells) genetically manipulated and cultured in vitro into tetraploid blastocysts and implanting the resulting embryo in a foster mother, in a single operation.

14 Claims, 3 Drawing Sheets

OTHER PUBLICATIONS

Figure 1:
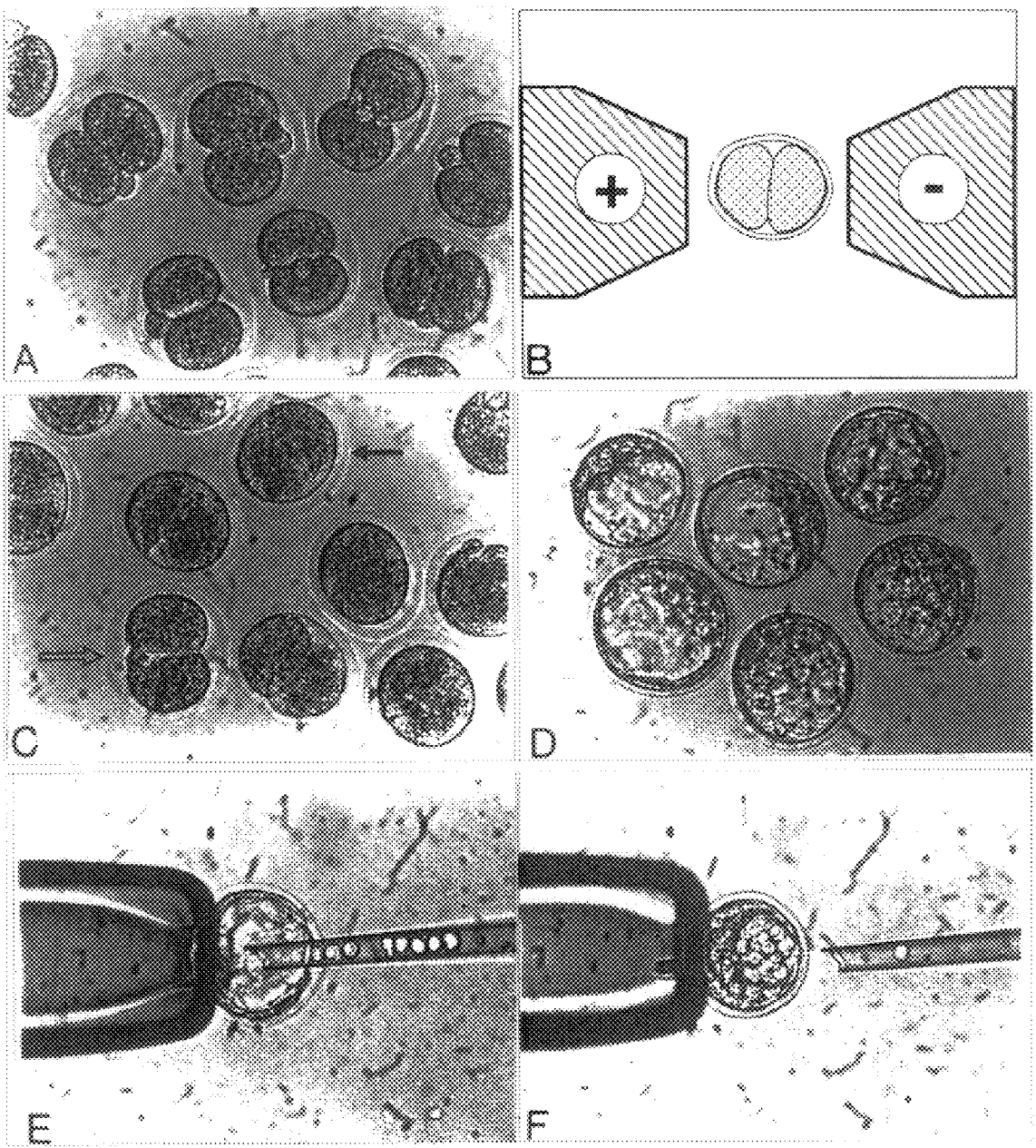

Bradley, A. and Robertson, E.J., "Injection of Cells into the Blastocyst," in *Manipulating the Mouse Embryo, A Laboratory Manual*, Hogan et al., eds., Cold Spring Harbor Laboratory Press, Cold Spring Harbor, NY, pp. 188–195 (1986).

Bronson, S.K. and Smithies, O., "Altering mice by homologous recombination using embryonic stem cells," *J. Biol. Chem.* 269:27155–27158 (1994).

Carmeliet, P. et al., "Abnormal blood vessel development and lethality in embryos lacking a single VEGF allele," *Nature* 380:435–439 (Apr. 1996).

Everett, C.A. and West J.D., "The influence of ploidy on the distribution of cells in chimaeric mouse blastocysts," *Zygote* 4:59–66 (Feb. 1996).

Gardner, R.L., "Mouse chimaeras obtained by the injection of cells into the blastocyst," *Nature* 220:596–597 (1968).

Hilberg, F. and Wagner, E.F., "Embryonic stem (ES) Cells lacking in functional c–*jun*: consequences for growth and differentiation, AP–1 activity and tumorigenicity," *Oncogene* 7:2371–2380 (1992).

James, R.M. and West, J.D., "A chimaeric animal model for confined placental mosaicism," *Human Genetics* 93:603–604 (1994).

James, R.M. et al., "Electrofusion of mouse embryos results in uniform tetraploidy and not tetraploid/diploid mosaicism," *Genet. Res.* 60:185–194 (1992).

James, R.M. et al., "Restricted distribution of tetraploid cells in mouse tetraploid⇌diploid chimaeras," *Dev. Biol.* 167:213–226 (Jan. 1995).

Kaufman, M.H. and Webb, S., "Postimplantation development of tetraploid mouse embryos produced by electrofusion," *Development* 110:1121–1132 (1990).

Kubiak, J.Z. and Tarkowski, A.K. "Electrofusion of mouse blastomeres," *Exp. Cell Res.* 157:561–566 (1985).

Nagy, A. and Rossant, J., "Production of completely ES cell–derived fetuses," in *Gene Targeting:A Practical Approach*, Joyner, A. L., ed., IRL Press, Oxford, pp. 147–179 (1993).

Nagy, A. et al., "Embryonic stem cells alone are able to support fetal development in the mouse," *Development* 110:815–821 (1990).

Nagy, A. et al., "Derivation of Completely Cell Culture–derived Mice from Early–passage Embryonic Stem Cells," *Proc. Natl. Acad. Sci. USA* 90:8424–8428 (1993).

Prather, R.S. et al., "Characterization of DNA Synthesis During the 2–cell Stage and the production of tetraploid chimeric pig embryos," *Molec. Reprod. Devel.* 45, 38–42 (Sep. 1996).

Ramírez–Solis, R. et al., "Gene targeting in embryonic stem cells," *Meth. Enzymol.* 225:855–878 (1993).

Skarnes, W.C., "The identification of new genes: gene trapping in transgenic mice," *Curr. Opin. Biotechnol.* 4:684–689 (1993).

Stewart, C.L. et al., "Expression of foreign genes from retroviral vectors in mouse teratocarcinoma chimaeras," *EMBO J.* 4:3701–3709 (1985).

Ueda, O. et al., "Production of mice entirely derived from embryonic stem (ES) cell with many passages by coculture of ES cells with cytochalasin B induced tetraploid embryos," *Exp. Anim.* 44:205–210 (Jul. 1995).

Urbánek, P. et al., "Complete block of early B cell differentiation and altered patterning of the posterior midbrain in mice lacking Pax5/BSAP," *Cell* 79:901–912 (1994).

Wagner, E.F. and Keller, G., "The Introduction of Genes into Mouse Embryos and Stem Cells," in *Development, The Molecular Genetic Approach*, Russo, V.E.A. et al., eds., Springer, Berlin, pp. 440–458 (1992).

Wang, Z.–Q. et al., "Generation of completely embryonic stem cell derived mice using tetraploid blastocyst injection," *Mech. Dev.* 62:137–145 (Mar. 1997).

Wang, Z.–Q et al., "A novel target cell for c–*fos*–induced oncogenesis: development of chondrogenic tumours in embryonic stem cell chimeras," *EMBO J.* 10:2437–2450 (1991).

Wood, S.A. et al., "Non–injection methods for the production of embryonic stem cell–embryo chimaeras," *Nature* 365:87–89 (1993).

MR Capecchi, Scientific American,"Targeted Gene Replacement," Mar. 1994, pp. 52–59.*

C. Stewart et al., "Rapid Communication Stem Cells from Primordial Germ Cells can reenter the Germ Line,"Developmental Biologh (1994) 161, pp. 626–628.*

Donovan et al, 1997, Transgenic Animals: Generation and Use, Harwood Pub., pp. 179–187.*

Moreadith et al, 1997, J. Mol. Med., 75: 208–216.*

Mullins et al, 1996, J. Clin. Invest., 98:S37–40.*

Hammer et al., 1986, Journal of Animal Science, 6: 269–278.*

Seamark, 1994, Reproduction, Fertility, and Development, 6:653–657.*

Wang et al, 1997, Mech. of Develop., 62: 137–145.*

Bradley et al, 1987, Teratocarcinomas and Embryonic Stem Cells, Oxford Press, 113–151.*

Ebert et al., 1988, Molecular Endocrinology, 2: 277–283.*

Houdebine et al., 1994, J. of Biotechnology, 34: 269–287.*

James et al, 1992, Genet. Res. Comb., 69: 184–194.*

Nagy et al, 1993, Gene Targeting: A practical Approach, IRL Press, 147–179.*

* cited by examiner

A. New-born

B. Adult

METHOD FOR DEVELOPING TRANSGENIC MICE

The invention relates to the production of mammals with defined genetic properties, particularly the production of transgenic animals.

Transgenic animals are organisms into whose germline permanent genetic changes have been introduced; a newly introduced gene is known as a transgene. Transgenic animals constitute an essential tool in modern biology for analysing the tissue-specific regulation of genes and their function in development and in diseases. Moreover, transgenic technology provides an opportunity of having animal models available for diseases in humans and producing large amounts of proteins in farm animals.

In the method of producing transgenic animals which has hitherto been used most frequently, recombinant DNA is microinjected into the fertilized eggs; another technique for introducing genes into animal embryos makes use of viruses, usually recombinant retroviral vectors (cf. the summarising articles by Wagner and Keller, 1992).

The third and most recent technique for introducing foreign genetic material into animals makes use of the potential of embryonic stem cells (ES cells) to create chimeric animals. Mammalian embryos have the capacity to incorporate foreign cells during their development. Two different pre-implantation embryos, usually morulae, are aggregated in vitro; this produces a chimeric embryo, which constitutes a mixture of the two embryos. These embryos are then transferred into a pseudo-pregnant mouse which acts as a foster mother; the chimeric offspring obtained have, in their tissues, different numbers of cells which originate from one of the two original embryos. Combining this method with the use of ES cells has proved very effective in the production of genetically manipulated animals.

Embryonic stem cells are derived from the inner cell mass (ICM) of blastocysts; they are totipotent cells which are capable of developing into all cell lineages, including germ cells, when introduced into an embryo by injection into diploid blastocysts or by aggregation with morulae (Robertson, 1987; Bradley, 1987; Beddington and Robertson, 1989; Nagy et al., 1990). ES cells can be isolated from blastocysts and then established as permanent cell lines if they are cultivated under well defined culture conditions which are strictly adhered to; they can be genetically manipulated. In view of this ability, they constitute an effective tool for modifying the mammalian and particularly the mouse genome by being introduced into the animals, for example, by means of controlled mutations or other genetic modifications (Wagner et al., 1991; Ramirez-Solis et al., 1993; Skarnes, 1993; Bronson and Smithies, 1994).

For some time, cells designated "embryonic germ cells" (EG cells) have been available, which can be cultivated from primordial germ cells into immortalised cell lines and are similar to ES cells in many respects; EG cells are, inter alia, totipotent, can be manipulated in the same way as ES cells and form germline chimeras when introduced into blastocysts (Donovan et al., 1997).

In recent years, various experimental techniques have been developed for producing animals derived from totipotent cells. (Totipotent cells are cells with the ability to differentiate themselves into all somatic cells as well as germ cells.) In the case of ES cells the primary objective of these methods was to obtain the entire developmental potential of ES cells in vitro (Williams et al., 1988; Smith et al., .1988) and to restrict the developmental potential of the host cells in the formation of chimeras and thus increase the frequency of forming germline chimeras (Nagy et al., 1990; Kaufman and Webb, 1990). One of the most important pieces of progress in the development of these techniques is the use of tetraploid embryos as host cells, because tetraploid cells have only restricted potential for development after they have been implanted (Nagy et al., 1990; Kaufmann and Webb, 1990; Kubiak and Tarkowski, 1985). When tetraploid embryos are aggregated with diploid embryos, the differentiation of the tetraploid cells is largely restricted to the primitive endoderm and the trophectoderm, which subsequently form extraembryonic tissue, whereas the diploid cells can form the actual embryo (James and West, 1994; James et al., 1995).

In an earlier study, various ES cell lines were aggregated with morulae in order to produce fetuses which are derived completely from ES cells (organisms derived completely from ES cells are hereinafter referred to as ES animals, e.g. ES mice or ES fetuses; however, the ES foetuses obtained died at birth (Nagy, 1990). Further studies showed that viable, fertile ES mice derived exclusively from ES cells can be obtained if wild-type R1 cells of an earlier passage (Nagy et al., 1993) or TT2 cell lines (Ueda et al., 1995) are used for the aggregation with tetraploid morulae.

Moreover, ES mice are produced by injecting ES cells into diploid blastocysts in a first step, thereby initially obtaining chimeric mice; further crosses produced ES mice after two generations. The method of injecting into blastocysts was first described by Gardner, 1968, and a simplified version was described by Bradley and Robertson, 1986, and by Bradley, 1987.

The objective of obtaining viable ES mice by using ES cells from later passages has not been achieved with the methods available hitherto (Nagy et al., 1993); it did not seem possible to produce ES mice at all using genetically modified ES cells. (The possibility of using ES cells from later passages is significant particularly in view of the use of cell lines and also with respect to the use of genetically modified ES cells the selection of which naturally goes hand in hand with an increase in the number of passages.)

The aim of the present invention was to provide a new process by which mammals with defined genetic properties, particularly transgenic mammals, can be obtained which are derived completely from totipotent cells.

The objective is achieved by means of a process for producing mammals with defined genetic properties, particularly transgenic mammals, wherein totipotent cells of the same mammalian species are introduced into blastocysts and the resulting embryo is transferred into a foster mother. The process is characterised in that totipotent cells with defined genetic properties are introduced into tetraploid blastocysts.

Using the process according to the invention it is possible to obtain animals which are completely derived from totipotent cells. The process according to the invention has the advantage that animals derived totally from totipotent cells are obtained in a single step from totipotent cells cultivated in vitro (ES cells or EG cells).

The term "transgenic mammals" includes, for the purposes of the present invention, animals which have a permanent genetic modification of any kind.

Animals which "are totally derived from totipotent cells" preferably contain up to 100% of cells originating from ES cells or EG cells. However, the animals may contain a small proportion, preferably not more than 10%, of cells derived from the tetraploid blastocysts.

In a preferred embodiment of the invention the mammals are mice; however, the process may also theoretically be applied to all mammals from which ES cells or EG cells can be obtained. The prerequisite for obtaining totipotent cells from mammals other than mice is the definition of conditions which allow the cultivation of ES cells or primordial germ cells from these organisms and the establishing of ES or EG cell lines, which include, inter alia, the need for specific growth factors as well as feeder cells for co-cultivation with the ES cells or EG cells. These conditions can be determined empirically by series of tests.

The isolation of ES cells from blastocysts, the establishing of ES cell lines and their subsequent cultivation are carried out by conventional methods as described, for example, by Doetchmann et al., 1985; Li et al., 1992; Robertson, 1987; Bradley, 1987; Wurst and Joyner, 1993; Hogen et al., 1994; Wang et al., 1992. The cultivation of EG cells can be carried out using methods described in the summarising article by Donovan et al., 1997, and in the original literature cited therein. Totipotent cell lines, e.g. mouse ES cell lines, can be tested in preliminary trials to see whether they are suitable for use in the present invention on the basis of their development potential. To find this out, cells of the lines in question may be injected into diploid mouse embryos, the resulting embryos are introduced into foster mothers and the young are examined for their chimerism rate and for the frequency of formation of germline chimeras.

In a preferred embodiment of the invention the totipotent cells are ES cells.

Tetraploid blastocysts may be obtained by known methods by electrofusion of two-cell embryos and subsequently cultured as described, for example, by James et al., 1992; Nagy and Rossant, 1993; or by Kubiak and Tarkowski, 1985.

The introduction of the ES cells or EG cells into the blastocysts is also carried out in a manner known per se. The preferred method for the purposes of the present invention is the microinjection method as described by Wang et al., 1991, for example. In conventional microinjection, about 5–10 ES cells taken from a single cell suspension are injected into a blastocyst immobilised by a holding pipette in a micromanipulation apparatus. Then the embryos are incubated for at least 3 hours, possibly overnight.

In a preferred embodiment of the invention, genetically manipulated totipotent cells are used in order to obtain transgenic animals.

There are no restrictions regarding the type of genetic alteration of the totipotent cells; genes may be overexpressed, mutated or, in order to produce so-called knock-out animals, switched off; furthermore, foreign genes may be inserted or intrachromosomal deletions may be carried out. The genetic modification may be carried out on one or both alleles; this latter approach has been described for example by Hilberg and Wagner, 1992, for switching off the c-jun gene. The fact that the present invention allows genetic modification on both alleles is particularly advantageous; with the methods of the prior art it was only possible to obtain transgenic animals in which both alleles had the desired modification, after further crossing and tedious breeding of animals which had a genetic modification on one allele.

The genetic manipulation of the totipotent cells may be carried out by conventional methods. Generally, plasmids are used, preferably linearised plasmids, which carry the desired genetic modification. With a view to the selectability of the genetically modified ES cells, the plasmids preferably contain a marker gene, e.g. the neomycin, hygromycin or puromycin resistance gene, under the control of a promoter. With a view to the expression of a gene contained on the plasmid in the host cells the plasmid may contain gene expression control sequences, e.g. a strong promoter which is functional in ES cells or EG cells, such as the PGK (phosphoglycerol kinase) promoter.

The methods by which the plasmid is introduced into the cells are standard methods known from the literature for in vitro transfer of DNA into mammalian cells, such as electroporation; calcium phosphate precipitation or methods based on receptor-mediated endocytosis, disclosed in WO 93/07283, for example.

Another method of introducing genetic changes in the totipotent cells makes use of viruses, e.g. recombinant retroviral vectors; with regard to sequence sections contained on the vector which allow the selection of genetically modified cells or expression in the cell, basically the same applies as has already been stated with regard to the plasmids (Wagner and Keller, 1992; Stewart et al., 1985).

Using the process according to the invention it is routinely possible to produce viable and fertile transgenic mammals, particularly ES or EG mice, from totipotent cells genetically modified in vitro.

Using the process according to the invention, transgenic animals can be reproducibly created, inter alia from genetically manipulated totipotent cells which overexpress a specific gene, for example, or in which a specific gene has been inactivated, and these transgenic animals may be used, inter alia, for studies of gene function or for the production of proteins. Compared with conventional methods of producing transgenic animals, the process according to the invention provides an effective, rapid and economical method of producing mutant animal foetuses, particularly mouse foetuses, as well as transgenic strains directly from totipotent cells in which the desired genetic modifications have been made.

All three ES cell lines designated D3, R1 and GS1 investigated for the purposes of the present invention formed germline chimeras after injection into diploid blastocysts. When they were injected into tetraploid blastocysts, live ES mice were obtained from R1 and GS1 cells. With D3 cells it was not possible to produce live ES mice, even with cells from an early passage (passage 9), after injection of ES cells into tetraploid blastocysts. This accords with previous observations from aggregation experiments (Nagy et al., 1990; see also Table 2) with these cells. The inability of D3 cells to form viable ES mice presumably cannot be put down to the fact that these cells have lost their development potential; D3 cells have frequently been used in so-called gene targeting experiments in which, after they have been injected into diploid blastocysts, a high rate of chimerism and germline chimeras have been obtained (Urbánek et al., 1994; Wang et al., 1992; Wang et al., 1994; cf. also Tab.1). However, it is possible that the potential of D3 cells to differentiate into a few cell types which are critical for adapting the foetus to post-natal life is affected by unknown genetic or epigenetic changes. This assumption is supported by the observation that D3 cells are capable of producing foetuses which develop up to the normal birth date but the newborn are incapable of maintaining breathing, and they have a high birth weight and polydactyly and die at birth. These characteristics remind one of the phenotypical features of mice which lack the imprinted Igf2/Mpr gene (Wang et al., 1994; Lau et al., 1994); it might therefore be the case that imprinted genes or genes which regulate the growth of the foetuses are responsible for the effect observed. Whereas in the environment of host cells of diploid embryos defective functions of the ES cells might be complemented by the host cells, the development potential of being able to form all functional cell types, which is inherent in the D3 cells because of their lack of differentiation, would appear to be restricted in an environment derived totally from ES cells. The introduction of different wild-type ES cells into tetraploid embryos, conveniently in series of tests, may therefore be used as a fast and reliable test for checking the suitability of ES cells for use within the scope of the present invention.

The genetic background of the mouse strains from which the various ES cells originate could be another factor which influences the viability of the ES mice. All the ES cell lines used within the scope of the present invention originated from mouse strain 129:the R1 cells originated from a mouse blastocyst from a cross between the sub-strains 129/Sv and 129/Sv-CP (Nagy et al., 1993); GS1 cells originated from 129/Sv/Ev. D3-cells (Doetchmann et al., 1985) and J1 cells (Li et al., 1992) originated from 129/Sv or 129/terSv. TT2 cells which also yielded ES mice originated from an F1 hybrid strain (C57BL/6×CBA) (Yagi et al., 1993). On the basis of the results obtained within the scope of the present invention as well as earlier studies (Nagy et al., 1993, Ueda et al., 1995) we cannot rule out the possibility that ES cell lines derived from different strains or sub-strains of mice have different capacities to form viable ES mice.

The efficiency in the production of newborn ES mice by injection of wild-type R1 cells into tetraploid embryos (14%) was greater than the production by aggregation (6% within the scope of the present invention or 7% in the study described by Nagy et al., 1993). These results are in agreement with a comparison between the aggregation method and the method by injecting ES cells into diploid embryos (Wood et al., 1993). The use of tetraploid blastocysts according to the invention for the injection method showed that some selected R1 cell clones which had been cultivated in vitro for longer than 24 passages (e.g. R169.2.3 and R-fra3), still had the ability to produce viable ES mice. These findings are remarkable, particularly in view of the results of earlier aggregation experiments in which wild-type R1 cells lost their ability to produce viable ES mice after passage 14 (Nagy et al., 1993). The reasons why the injection of ES cells into tetraploid blastocysts reproducibly leads to the formation of ES mice are not totally clear. Since ES cells are obtained originally from ICM of blastocysts and are also very similar to these ICM cells (Beddington and Robertson, 1989), it is conceivable that both the spatial proximity of ES cells and ICM and their compatibility in development are responsible for this effect. This assumption is further supported by the observation, comparison tests, that the efficiency of producing chimeric mice was lower when ES cells were introduced into diploid morulae below the "zona pellucida" than when the conventional blastocyst injection method was used (injection into diploid blastocysts).

The high efficiency of the method according to the invention makes it superior to the methods of the prior art (aggregation of ES cells with tetraploid blastocysts or injection into diploid blastocysts) and offers the only possible method at present of creating mutant mice directly from genetically modified totipotent cells.

The production of viable mutant mice directly from genetically manipulated totipotent cells has numerous advantages. Since the foetal tissues are derived totally from totipotent cells which can be genetically modified, this technique provides a direct method of producing foetal material of pure ES or EG cell origin for cell-biological, molecular-biological or genetic studies (Forrester et al., 1991; Carmeliet et al., 1996).

ES foetuses reproduce the expression patterns of specific genes, such as for example the Pax5 gene or a "trapped" gene, in a reliable manner, compared with foetuses produced by crossing heterozygotic mutant mice obtained from the same ES cells. Advantageously, ES foetuses can be used for expression studies, since they allow rapid production of foetal material (a few days) whereas conventional breeding normally takes four to five months. In addition, the reliable and reproducible expression pattern in ES foetuses minimises any possible complications in conventional chimeric tissues which by definition consist of both wild-type and mutated ES cells. Therefore, this technique is useful for studying gene function or for identifying new genes, e.g. in "gene-trap" studies (Skarnes, 1993). It has been shown that, with the aid of the method according to the invention (injection of ES cells into tetraploid blastocysts), mutant mouse lines, e.g. c-fos transgenes and fra-1 "knock-out" mice can be produced directly from mutant ES cells in an efficient manner. The process according to the invention makes it possible to produce transgenic mouse lines from ES cells or EG cells which had been preselected for the integration and expression of transgenes. The efficiency of producing mice which overexpress a specific gene is thereby improved significantly, compared with the conventional injection method in which diploid blastocysts are used. The process according to the invention has been used in a number of studies into gene overexpression and inactivation.

Furthermore, using this method, it is possible to produce mutant tissue for studying specific effects if inactivation or overexpression should lead to death or impaired gametogenesis in heterozygotic mutants or even in chimeras (see for example Carmeliet et al., 1996).

Finally, the process according to the invention offers the possibility of producing mutant animal strains, particularly breeds of mice, rapidly and economically and of having quick access to mutant foetuses and animals, which is a major advantage for research in the field of mice genetics.

As well as the production of transgenic animals, the process according to the invention may also be used to produce non-genetically modified ES animals or EG animals which have specific desirable qualities. For this, totipotent cells are used which are preselected for the desired qualities by culture experiments, in order to obtain identical animals with the required qualities.

LIST OF FIGURES

FIG. 1: Production of tetraploid embryos. Injection of ES cells into tetraploid-blastocysts (Panels A–F)

Figure 2:
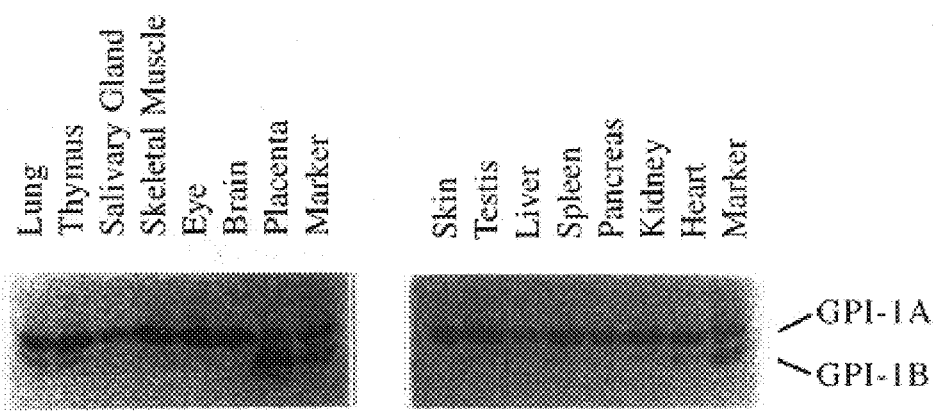
Figure 2:
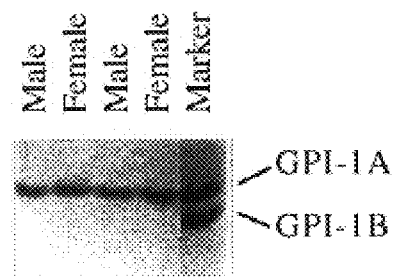

FIG. 2: GPI analysis of newborn ES mice (Panel A) and offspring of ES mice originating from R1 cells (Panel B)

Figure 3:
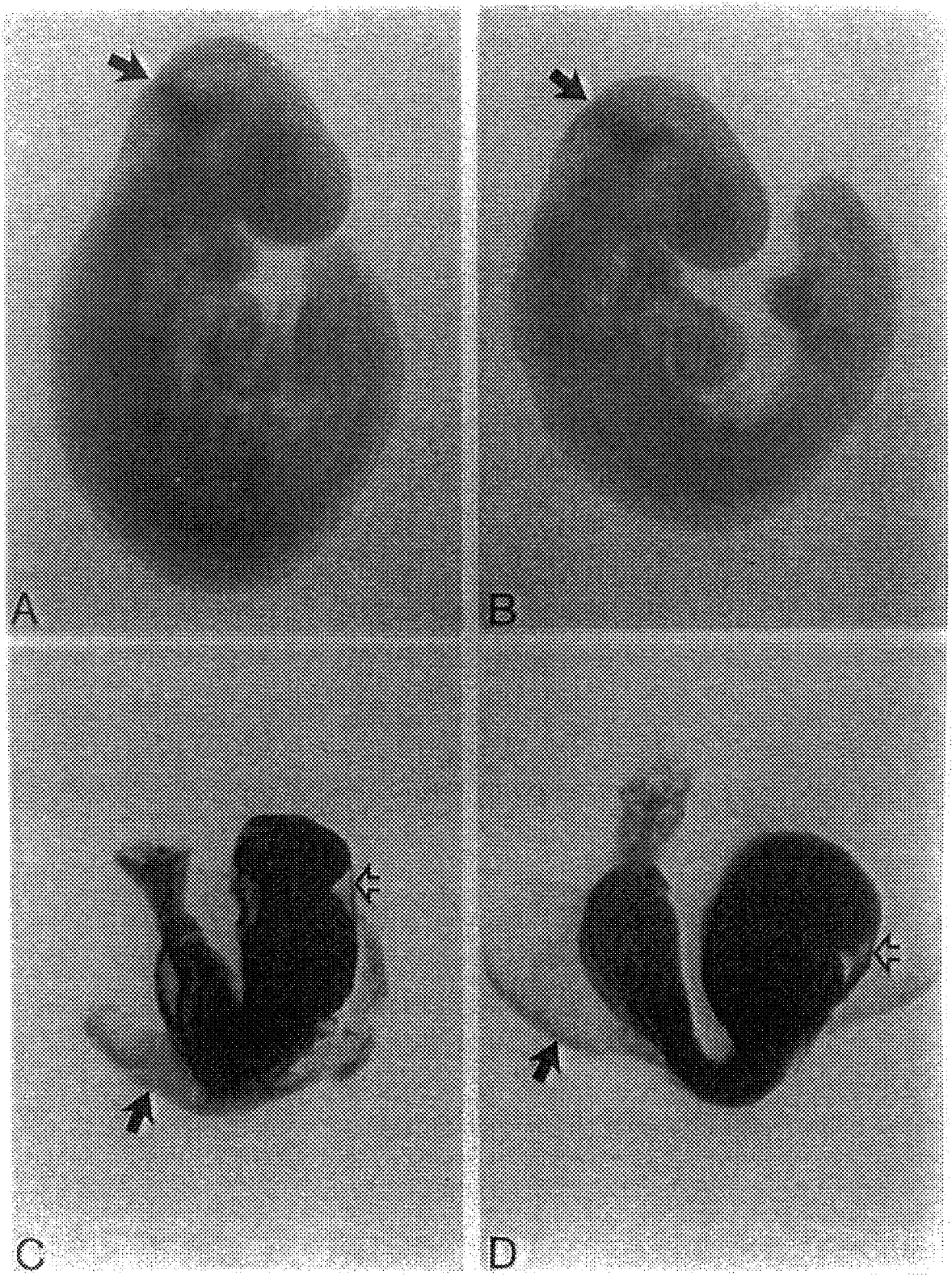

FIG. 3: Comparison of lacZ gene expression in ES fetuses (Panel A, C) and in foetuses originating from heterozygotic crosses (Panels B, D).

In the Examples which follow, illustrating the present invention, the following materials and methods were used unless otherwise specified:

a) Mice

C57BL/6 mice were used as the donors of diploid embryos and B6CBAF1 mice (C57BL/6×CBA) were used as donors of tetraploid embryos. Both-strains are homozygous for the Gpi-$1^b$ allele at the Gpi-1 locus which codes for glucose phosphate isomerase (GPI).

b) ES Cells and Gene Transfer: the Following ES Cells Described in the Literature were Used D3 cells (Doetchmann et al., 1985) R1 cells (Nagy et al., 1993) J1 cells (Li et al., 1992)

GS1 cells were isolated from blastocysts of the substrain 129/Sv/EV. This mouse strain was established from a chimeric mouse obtained after germline transfer of ES cells of the genotype of AB1. AB1-ES cells were originally established from substrain 129/Sv/EV, as described by McMahon and Bradley, 1990, and by Papaioannou, 1993. The GS1 cells were essentially isolated using the method described by Robertson, 1987, blastocysts were plated out on a 4-well plate on feeder cells and the ICM increased after 5 days' culture. The clumps resembling ES cells were broken up with a pipette and plated out again on a new plate with feeder cells. The expanded ES cells were identified and further investigated to discover their karyotype and their totipotency in view of their development.

All the ES cells were originally isolated from the replication of blastocysts obtained from mouse strain 129, which is homozygotic for the Gpi-$1^a$ allele. In order to modify the ES cells, R1 cells from passage 16 were electroporated with various constructs; G418-resistant clones were selected and expanded before the injection. The following constructs were used: a c-fos overexpressing vector (Wang et al., 1991); a so-called "gene-trap vector" designated pSAβgeo which contains a lacZ-neo fusion gene without a promoter and which has the ability to integrate into introns of any genes (Friedrich and Soriano, 1991); a so-called gene targeting vector which interrupts the Pax5 gene by homologous recombination in mice (Urbánek et al., 1994); and a gene targeting vector which interrupts the endogenous fra-1 gene (Fos related antigen 1) by homologous recombination. (In order to prepare the fra-1 "gene targeting vector", some cosmid clones which contain the fra-1 gene were isolated from a genomic mouse library, and the sequence and exon/intron organisation of the gene as a whole were determined. On the basis of this information, a zero mutation in the fra-1 gene was introduced by homologous recombination into ES cells.

Starting from the plasmid pGNA (Le Mouellic et al., 1990; 1992) a gene targeting vector was constructed. In this vector the essential DNA binding and dimerising (leucine zipper) domains of fra-1 were replaced by the bacterial genes coding for β-galactosidase and neomycin resistance which act as reporter genes or selectable markers in mammals. After the electroporation of ES cells, G418-resistant colonies were analysed either by Southern blot or by staining for their β-galactosidase activity in order to confirm the integration of the vectors.

c) Obtaining Two-cell Embryos; Electrofusion

Two-cell embryos were isolated from female B6CBAF1 mice on day 1.5 post-coitum (p.c.) and used for the production of tetraploid blastocysts (FIG. 1A). Tetraploidy of the embryos was brought about by electrofusion, by a modified version of the method described by Nagy and Rossant (1993) : two-cell embryos were equilibrated for 30 seconds in a 0.3M mannitol solution before being individually arranged between two platinum electrodes in 0.3M mannitol and exposed to a short current surge at 95V for 30 μsec in an effective field of 2V using a current surge generator CF-100 (Biochemical Laboratory Service, Budapest) (FIG. 1B). After an incubation period of 15 minutes, two blastomers began to fuse (FIG. 1C, open arrow) and gradually to form a single cell embryo (FIG. 1C, arrow).

d) Aggregation of ES Cells with Morulae; Injection of ES Cells into Blastocysts

For aggregation the morulae were either isolated from the Fallopian tubes of pregnant mice (day 2.5 p.c.) or obtained from tetraploid single cell embryos by cultivating them 24 to 40 hours after electrofusion. The processing and aggregation of the ES cells were carried out as described by Nagy et al. (1990). Diploid blastocysts were isolated from the uterus of pregnant C57BL/6 mice (day 3.5 p.c.). In order to obtain tetraploid blastocysts, the electrofused single cell embryos were cultivated 48 to 60 hours after fusion (M16 medium at 37° C. in an incubator with 95% air/5% $CO_2$; FIG. 1D). Wild-type or gene-manipulated ES cells were then injected, by the method described by Wang et al. (1991), into diploid or tetraploid blastocysts (FIG. 1E, FIG. 1F). Whereas the injected diploid embryos developed in the normal gestation time and were then delivered naturally, the pregnant mice which had been given the tetraploid embryos were subjected to caesarian section on day 18.5 (Nagy et al., 1990). Viable foetuses, assessed on the basis of heartbeat and respiration, were reared by a female which had given birth on the same day or on the day before. Some of the live young were examined for GPI markers. The surviving ES mice were further paired with wild-type C57BL/6 mice to test them for fertility and inheritance of germline.

e) GPI-isoenzyme Analysis

Various tissues from foetuses or adult animals originating from ES cells were isolated and ground up in distilled water. The samples were lysed by three freezing/thawing cycles and subjected to GPI analysis after protein extraction, as described by Bradley (1987) and Wang et al. (1991). In the chimeric tissues the proportion of cells which originated from ES cells or from the host was estimated from the ratio of GPI-1A or GPI-1B isoenzyme activity which was demonstrated in a coupled optical assay.

f) β-Galactosidase Histochemistry

A modified version of the method described by Sanes et al. (1996) was used to determine the β-galactosidase activity in fixed intact embryos. The embryos and their extra-embryonic membranes were fixed for 5–10 minutes (100 mM Na-phosphate, pH 7.4, 5 mM EGTA, 2 mM $MgCl_2$, 0.2% glutaraldehyde), then washed three times (100 mM Na-phosphate, pH 7.4, 2 mM $MgCl_2$ 0.01% Na-deoxycholate, 0.02% NP-40) and stained with a histochemical reaction mixture (100 mM Na-phosphate, pH 7.4, 2 mM $MgCl_2$ 0.01% Na-deoxycholate, 0.02% NP-40, 5 mM K-iron(III)-cyanide, 5 mM K-iron(II)-cyanide and 1 mg/ml X-Gal).

EXAMPLE 1

Preparation of chimeric Mice Originating from Diploid Embryos and Wild-type ES Cells In order to test the developmental potential of different ES cell lines, first four different wild-type ES cell lines were used to produce chimeric mice, on the one hand by aggregation of the ES cells with diploid morulae and on the other hand by injecting them into diploid blastocysts. All four ES cell lines were shown to be capable of delivering a high rate of chimerism and of forming germline chimeras with great frequency after being introduced into diploid mouse embryos (see Table 1). Interestingly, a high proportion of female chimeras were also obtained with R1 and J1 cells, some of which passed on the agouti-coloured fur of the strain 129/Sv to their descendants (Table 1).

EXAMPLE 2

Production of Viable ES-mice By Aggregation of ES Cells with Tetraploid Embryos or Injecting the Cells into Blastocysts In order to produce tetraploid embryos, two-cell embryos received a brief surge of current which led to the fusion of about 90% of the embryos. These embryos were further cultivated. Five experiments were carried out in which the embryos developed with high frequency into morulae (68–95%) and blastocysts (80–98%). The morulae were used for aggregation with ES cells and the blastocysts were used for injecting ES cells into them (FIG. 1E, FIG. 1F). All four wild-type ES cell lines (D3, R1, J1 and GS1) were tested with regard to the production of ES mice. From the aggregation with D3 cells, 26 live newborn were obtained after caesarian section but not one of them survived (Table 2). Similarly, no viable ES mice could be obtained from J1 cells (Table 2). By contrast, R1 cells, after aggregation with tetraploid morulae, yielded ES mice with a frequency similar to that described by Nagy et al., 1993 (see Table 2).

Since the method of injecting ES cells into diploid blastocysts was about as efficient in terms of chimera formation as the aggregation method (cf. also Wood et al., 1993), first of all an investigation was carried out to see whether ES mice can be obtained by injecting wild-type ES cells into tetraploid blastocysts. When using D3 cells from passage 9, a relatively high proportion (28%) of fully developed foetuses were obtained by caesarian section on day 18.5 p.c. (E18.5) (Table 2); however, the neonates were unable to maintain their breathing and died shortly afterwards. Interestingly, these neonates had a higher body weight and suffered from polydactyly. Of 36 tetraploid blastocysts which had been injected with R1 cells (passage 14), nine viable young were born by caesarian section at the time E18.5 (Table 2). Five of them were able to maintain their breathing and were reared by a foster mother. Regrettably, two of the young could not be found after 7 days and one died at the age of 5 weeks. Two of these ES mice survived to adulthood and demonstrated total inheritance of the germline (Table 2). After the injection of GS1 cells into 54 tetraploid blastocysts, 17 embryos developed in the normal gestation period (Table 2). Six young were born by caesarian section and were able to maintain their breathing. Five young died within 48 hours and one ES mouse survived to adulthood and passed the genetic material originating from ES cells on to its descendants (Table 2).

EXAMPLE 3

Production of ES Mice with Genetically Modified ES Cell Clones

After viable ES mice had been produced from tetraploid blastocysts into which the R1 or GS1 wild-type cells had been injected, the next test was to find out whether the method according to the invention is also suitable for yielding mutant ES mice from genetically manipulated ES cells. First, R1 cells were electroporated with the c-fos expression vector and two G418-resistant clones designated R-169.2.3 and R-169.2.5 were used for injection into tetraploid blastocysts (the R1 clones were cultivated over more than 24 passages before being injected into blastocysts). Clone R-169.2.5 was injected into a total of 103 blastocysts; twelve neonates were obtained by caesarian section. Three of them maintained their breathing but died after 48 hours. Clone R-169.2.3 yielded a higher number of surviving neonates; 23 young were viable after caesarean section and 12 of them were reared by a foster mother (Table 2). Unfortunately, seven neonates died in the first three days as a result of inadequate care by their foster mother. Two other mice were lost during the weaning phase. Three mice survived to adulthood. After it had been confirmed by Southern blot analysis that the transgene had been passed on to the descendants, two transgenic lines were established.

In a further experiment, an R1 clone designated R-fra 3 (fra-1 +/−) from passage 24 was used in which an allele of the fra-1 gene is interrupted by homologous recombination. R-fra 3 cells were injected into 48 tetraploid blastocysts; eight live young were obtained by caesarian section. Four out of five neonates reared by a foster mother reached adulthood, and three of them were shown to have passed the mutated allele (fra-1 +/−) on to their descendants (Table 2). The female chimeric mouse was sterile, which conflicted with the results obtained with wild-type R1 cells, where chimeric females capable of producing germline descendants were obtained with these cells and diploid embryos.

EXAMPLE 4

GPI Analysis in Tissues of ES Foetuses and ES Mice

In order to confirm that the foetuses and adult mice obtained according to the preceding Examples actually originated exclusively from ES cells, a GPI analysis was carried out by means of which the contribution of the ES cells to tissue formation can be determined. From the experiments in which aggregation had been carried out, all eleven foetuses from D3 cells, one from R1 cells and one from J1 cells showed 100% descent from ES cells in all the tissues investigated (Table 3) A foetus derived from R1 cells had a small proportion of tissue (about 10%) in its heart which was derived from host cells, but the other tissues investigated were derived exclusively from ES cells (FIG. 2A, Table 3). Similarly, most of the ES foetuses and all the adult ES mice derived from R1 and GS1 which had been produced by injecting the cells into tetraploid blastocysts originated exclusively from ES cells, with the exception of two of the D3-derived foetuses (E18.5) which showed a host cell contribution of 10 to 50% in their heart, lung and liver. Remarkably, four foetuses derived from R1 cells showed only the ES-specific GPI-1A marker at an early stage (day 13.5 p.c.) (Table 3). In addition, the descendants of the ES mice derived from R1. were examined by GPI analysis, showing that they originated from ES cells.

ES foetuses and adult mice which had been produced by injecting genetically modified R1 cells into tetraploid blastocysts were also examined by GPI analysis. Tissue from two newborn young (E18.5) which were derived from the ES clone R-169.2.5 were found to originate totally from ES cells. The GPI analysis of three day old young (derived from D3 cells) and adult mice which had been produced with R1 cells which either overexpressed a c-fos transgene (R-169.2.3) or which contained an inactivated allele of fra-1 (R-fra 3) showed in all the tissues investigated that they originated 100% from ES cells (Table 3). Moreover, GPI and Southern blot analyses were carried out on the descendants of these ES mice. It was confirmed that only the GPI-1A marker was present in all the offspring; some inherited either the transgene (c-fos) or the interrupted allele fra-1. FIG. 2A shows the GPI analysis of newborn ES mice derived from R1 cells. All the tissues, apart from the placenta and heart, contained only the GPI-1A marker, which indicates 100% descent from ES cells. FIG. 2B shows the GPI analysis of the offspring of an ES mouse: the blood from four young of an adult ES mouse contained only the GPI-1A isoenzyme confirming that the descendants were derived from ES cells.

EXAMPLE 5

Comparison of the Gene Expression Patterns of ES Cell Embryos and Germline Embryos In order to investigate the suitability of the process according to the invention for producing ES mice for investigating gene expression and mutant phenotypes, tests were carried out to determine when and where specific genes are expressed in ES cell embryos and in germline embryos. For this investigation, two genetically manipulated ES cell clones containing the lacZ reporter gene were selected, one of which led to a highly restricted lacZ expression pattern (Pax5 +/− ES clone D3-15; Urbánek et al., 1994); whilst the other yielded an extended β-galactosidase coloration (see below). FIG. 3 shows a comparison of the lacZ gene expression in ES foetuses (FIGS. 3A,C) with that in foetuses originating from heterozygotic crosses (FIGS. 3B,D). E9.5 embryos obtained from tetraploid blastocysts which had been injected with the clone D3-15 displayed specific expression of the lacZ gene at the interface between the central and hind brain (FIG. 3A, arrow). This staining pattern was identical with that of embryos obtained from heterozygotic crosses (FIG. 3B; cf. also Urbánek et al., 1994). The second ES clone investigated was an R1 clone designated R-βgeo3, which was obtained from a gene trap experiment. R-βgeo3 cells were injected into diploid and tetraploid blastocysts. The diploid embryos injected yielded fertile chimeras, some of them passed the lacZ transgene on to their descendants. It took about four to five months to establish a transgenic mouse line of this kind and have access to embryos from heterozygotic crosses. Embryos obtained by injecting R-βgeo3 cells into tetraploid blastocysts were isolated on day 8.5 and stained for β-galactosidase activity. Intensive coloration was detected throughout the entire embryo, in the amniotic membrane (FIG. 3C, open arrow) and allantoid membrane, but not in the umbilical vesicle (FIG. 3C, arrow). This staining pattern was identical to the staining pattern in heterozygotic embryos obtained after heterozygotic crossing (FIG. 3D). These results show that the expression pattern of the transgene is reliably maintained in ES mice via germline inheritance.

TABLE 1

Chimeric mice produced from diploid embryos which had been aggregated or injected with wild-type ES cells

| Cell lines | Number of embryos transferred | Number of mice born | Chimeras Number | M/F | Rate of chimerism (range) | Germline/tested |
|---|---|---|---|---|---|---|
| Aggregation: | | | | | | |
| D3 | 15 | 3 | 2 | 2/0 | 2M = 90–95% | 1/1 |
| Injection: | | | | | | |
| D3 | 69 | 47 | 31 | 30/1 | 26M = 95–100% | 22/24 |
| | | | | | 4M = 80–90% | 3/4 |
| | | | | | 1F = 90% | 0/1 |
| R1 | 24 | 14 | 12 | 7/5 | 7M = 95–100% | 5/5 |
| | | | | | 5F = 95–100% | 3/4 |
| J1 | 60 | 32 | 22 | 6/16 | 6M = 95–100% | 6/6 |
| | | | | | 9F = 95–100% | 3/8 |
| | | | | | 2F = 80–90% | 1/2 |
| | | | | | 5F = 10–50% | 2/5 |
| GS1 | 15 | 4 | 4 | 4/0 | 4M = 95–100% | 4/4 |

M: male animals; F: female animals;

TABLE 2

ES-mice produced from tetraploid embryos which had been aggregated or injected with modified ES-cells

| | ES-clones | Number of passages | Number of embryos transferred | Live young after caesarian section proportion (in %) | Number of surviving young (proportion in %) | Adult ES mice number | M/F | Germline/tested |
|---|---|---|---|---|---|---|---|---|
| Aggregation: | D3 | p9 | 159 | 26 (16%) | 0 | | | |
| | J1 | p11 | 37 | 1 (3%) | 0 | | | |
| | R1 | p14 | 88 | 14 (16%) | 5 (6%) | 4 | 4/0 | 2/2 |
| Injection: | D3 | p9 | 69 | 19 (28%) | 0 | | | |
| | R1 | p14 | 36 | 9 (25%) | 5 (14%) | 2 | 2/0 | 2/2 |
| | GS1 | p8 | 54 | 17 (31%) | 6 (11%) | 1 | 1/0 | 1/1 |
| | R-169.2.3 | p24 | 80 | 23 (29%) | 12 (15%) | 3 | 2/1 | 2/3 |
| | R-fra 3 | p24 | 48 | 8 (17%) | 5 (10%) | 4 | 3/1 | 3/4 |

M: male animals; F: female animals.

TABLE 3

Glucose phosphate isomerase (GPI)-Analysis of ES mice.

| ES-Mice | Age | Number of mice | Liver | Lung | Heart | Intestine | Brain | Skin | Spleen | Stomach | Kidney | Muscle | Testes | Blood | Extremities |
|---|---|---|---|---|---|---|---|---|---|---|---|---|---|---|---|
| Aggregation: | | | | | | | | | | | | | | | |
| D3 | E16.5 | 3 | 100 | — | — | — | 100 | — | — | — | — | — | — | — | 100 |
|  | E18.5 | 8 | 100 | — | — | — | 100 | — | — | — | — | — | — | — | 100 |
| R1 | E18.5 | 1 | 100 | 100 | 100 | 100 | — | 100 | 100 | — | 100 | 100 | 100 | — | 100 |
|  | E18.5 | 1 | 100 | 100 | 90 | 100 | — | 100 | 100 | — | 100 | 100 | 100 | — | 100 |
| J1 | E18.5 | 1 | 100 | 100 | — | — | 100 | — | — | — | — | — | — | — | 100 |
| Injection: | — | | | | | | | | | | | | | | |
| D3 | E18.5 | 11 | 100 | 100 | 100 | — | 100 | — | — | — | — | — | — | — | — |
|  |  | 1 | 70 | 80 | 90 | — | 100 | — | — | — | — | — | — | — | — |
|  |  | 1 | 50 | 50 | 60 | — | 100 | — | — | — | — | — | — | — | — |
| R1 | E13.5 | 4 | 100 | 100 | 100 | — | 100 | — | — | — | — | — | — | — | — |
|  | E18.5 | 4 | 100 | 100 | — | 100 | 100 | — | — | — | — | — | — | — | — |
|  | adult | 2 | 100 | 100 | 100 | 100 | 100 | — | 100 | 100 | 100 | 100 | 100 | 100 | — |
| GS1 | E18.5 | 8 | 100 | 100 | 100 | 100 | 100 | 100 | — | — | — | — | — | — | — |
|  | adult | 1 | 100 | 100 | 100 | 100 | 100 | — | 100 | 100 | 100 | 100 | 100 | 100 | — |
| MTc-fosLTR | | | | | | | | | | | | | | | |
| R-169.2.3 | P3 | 1 | 100 | 100 | — | 100 | 100 | 100 | — | — | 100 | — | 100 | 100 | — |
|  | adult | 3 | 100 | 100 | 100 | 100 | 100 | — | 100 | 100 | 100 | 100 | 100 | 100 | — |
| fra-1+/− | | | | | | | | | | | | | | | |
| R-fra3 | adult | 1 | 100 | 100 | 100 | 100 | 100 | — | 100 | 100 | 100 | 100 | 100 | 100 | — |

E13.5, E16.5 and E18.5: 13.5, 16.5 and 18.5 days, respectively, after the start of the pregnancy; P3: 3 days after birth.

BIBLIOGRAPHY

Beddington, R. S. P., & Robertson, E. J. (1989) *Development* 105, 733–737.

Bradley, A. (1987) in *Teratocarcinomas and Embryonic Stem Cells: A practical approach*, ed. Robertson, E. J. (IRL Press, Oxford Washington DC), 113–151.

Bradley, A. and Robertson, E. J., 1968, in *Manipulating the mouse embryo*, A Laboratory Manual. eds. Hogan, R., Constantini, F. and Lacy, E. (Cold Spring Harbor Laboratory Press), 188–195

Bronson, S. K., & Smithies, O. (1994) *J. Biol. Chem.* 269, 27155–27158.

Carmeliet, P., Ferreira, V., Breier, G., Pollefeyt, S., Keickens, L., Gertsenstein, M., Fahrig, M., Vandenhoeck, A., Harpal, K., Eberhardt, C., Declercq, C., Pawling, J., Moons, L., Collen, D., Risau, W., & Nagy, A. (1996) *Nature* 380, 435–439.

Chambers, C. A., Kang, J., Pawling, J., Huber, B., Hozumi, N., & Nagy, A. (1994) *Proc. Natl. Acad. Sci. USA*. 91, 1138–1142.

Doetchmann, T. C., Eistetter, H., Katz, M., Schmidt W., & Kemler, R. (1985) *J. Embryol. Exp. Morph.* 87, 27–45.

Donovan, P. J., et al., 1997, Transgenic Animals, Generation and Use, Editor: L. M:Houdebine, pp 179–187, Harwood Academic Publishers.

Forrester, L. M., Bernstein, A., Rossant, J., & Nagy, A. (1991) *Proc. Natl. Acad. Sci. USA* 88, 7514–7517.

Friedrich, G., & Soriano, P. (1991) *Genes & Dev.* 5, 1513–1523

Gardner, 1968, *Nature* 220, 596–597

Hilberg, F. & Wagner, E. F. (1992) *Oncogene* 7, 2371–2380

Hogan, B., Beddington, R., Costantini, F. & Lacy, E. (1994) in *Manipulating the Mouse Embryo: A laboratory manual*, eds. Hogan, B., Beddington, R., Costantini, F. & Lacy, E. (Cold Spring Harbor Laboratory Press) pp. 253–290)

James, R. M., & West, J. D. (1994) *Hum. Genet.* 93, 603–604.

James, R. M., Kaufman, M. H., Webb, S., & West, J. D. (1992) *Genet. Res. Camb.* 60, 185–194.

James, R. M., Klerkx, A. H. E. M., Keighren, M., Flockhart, J. H., & West J. D. (1995) *Dev. Biol.* 167, 213–226.

Kaufman, M. H., & Webb, S. (1990) *Development* 110, 1121–1132.

Kubiak, J. Z., & Tarkowski, A. K. (1985) *Exp. Cell Res.* 157, 561–566.

Lau, M. M. H., Stewart, C. E. H., Liu, Z., Bhartt, H., Rotwein, P., & Stewart, C. L. (1994) *Genes & Dev.* 8, 2953–2963.

Le Mouellic, H., Lallemand, Y. and Brulet, P. (1990) *Proc. Natl. Acad. Sci. USA* 87, 4712–4716.

Le Mouellic, H., Lallemand, Y. and Brulet, P. (1992) *Cell* 69, 251–264.

Li, E., Bestor, T. H., & Jaenisch, R. (1992) *Cell* 69, 915–926.

McMahon, A. P. and Bradley, A., 1990, *Cell* 62, 1073–1085.

Nagy, A., & Rossant, J. (1993) in *Gene Targeting: A practical approach*, ed, Joyner, A. L. (IRL Press, Oxford New York Tokyo), pp. 147–180.

Nagy, A., Góczá, E., Diaz, E. M., Prideaux, V. R.s, Iványi, E., Markkula, M., & Rossant, J. (1990) *Development* 110, 815–821.

Nagy, A., Rossant, J., Nagy, R., Abramow-Newerly, W., & Roder, J. (1993) *Proc. Natl. Acad. Sci. USA* 90, 8424–8428.

Papaioannou, V. and Johnson, R., 1993, in *Gene Targeting: A practical approach*, ed. Joyner, A. L. (IRL Press, Oxford, New York, Tokyo) 147–180

Ramirez-Solis, R., Davis A. C., & Bradley, A. (1993) *Methods Enzymol.* 225, 855–878.

Robertson, E. J. (1987) in *Teratocarcinomas and Embryonic Stem Cells: A practical approach*, ed. Robertson, E. J. (IRL Press, Oxford Washington DC), pp. 71–112.

Sanes J. R., Rubenstein J. L. R., & Nicolas, J.-F., 1986, *EMBO J.* 5, 3133–3142.

Skarnes, W. C. (1993) *Current Opinion in Biotech.* 4, 684–689.

Smith, A. G., Heath, J. K., Donaldson, D. D., Wong, G. G., Moreau, J., Stahl, M., & Rodgers, D. (1988) *Nature* 336, 688–690.

Stewart, C. L., Vanek, M. & Wagner, E. F. (1985) *EMBO Journal* 4, 3701–3709.

Ueda, O., Jishage, K., Kamada, N., Uchida, S., & Suzuki, H. (1995) *Jikken-Dobutsu* 44, 205–210.

Urbánek, P., Wang, Z.-Q., Fetka, I., Wagner, E. F., & Busslinger, M. (1994) *Cell* 79, 901–912.

Wagner, E. F., Wang, Z.-Q., Grigoriadis, A. E., Möhle-Steinlein, U., Aguzzi, A., & Risau, W. (1991) in *Origins of Human Cancer: A Comprehensive Review*, (Cold Spring Harbor Laboratory Press), 815–823.

Wagner, E. F. & Keller, G. (1992) in *Development, The Molecular Genetic Approach*, (Springer, Heidelberg), pp. 440–458.

Wang, Z.-Q., Fung, M. R., Barlow, D. P., & Wagner, E. F. (1994) *Nature* 372, 464–467.

Wang, Z.-Q., Grigoriadis, A. E., Möhle-Steinlein, U., & Wagner, E. F. (1991) *EMBO J.* 10, 2437–2450.

Wang, Z.-Q., Ovitt, C., Grigoriadis, A. E., Möhle-Steinlein, U., Ruther, U. & Wagner, E. F. (1992) *Nature* 360, 741–744.

Williams, R. L., Hilton, D. J., Pease, S., Willson, T. A., Stewart, C. L., Gearing, D. P., Wagner, E. F., Metcalf, D., Nicola, N. A., & Gough, N. M. (1988) *Nature* 336, 684–687.

Wood, S. A., Allen, N. D., Rossant, J., Auerbach, A., & Nagy, A. (1993) *Nature* 365, 87–89.

Wurst, W. & Joyner, A. L. (1993) in *Gene Targeting: A practical approach*, ed. Joyner, A. L. (IRL Press, Oxford New York Tokyo), pp. 147–180.

Yagi, T., Tokunaga, T., Furuta, Y., Nada, S., Yoshida, M., Tsukada, T., Saga, Y., Takeda, N., Ikawa, Y., & Aizawa, S. (1993) *Anal. Biochem.* 214, 70–76.

We claim:

1. A method for producing a transgenic mouse with a desired genotype, said method comprising:

(a) obtaining a mouse tetraploid blastocyst;

(b) introducing a plurality of mouse totipotent cells into said tetraploid blastocyst, wherein said totipotent cells have been genetically manipulated to comprise a transgene conferring a desired genotype to said cells, thereby producing a transgenic embryo; and (c) transferring said embryo into a foster mother under conditions favoring the development of said embryo into a transgenic mouse comprising said desired genotype.

2. The method of claim 1, wherein said blastocyst is obtained by electrofusion of two-cell embryos and subsequent culturing.

3. The method of claim 1, wherein said totipotent cells are embryonic stem cells.

4. The method of claim 1, wherein said totipotent cells are embryonic germ cells.

5. The method of claim 1, wherein said totipotent cells are introduced into said tetraploid blastocyst by microinjection.

6. The method of claim 1, wherein said totipotent cells were obtained by the introduction of plasmids which carry the desired genetic modification.

7. The method of claim 1, wherein said totipotent cells comprise at least one transgene.

8. A method for producing a transgenic mouse, comprising:

(a) obtaining a mouse tetraploid blastocyst by electrofusion of two-cell diploid embryos obtained from mouse;

(b) genetically manipulating mouse embryonic stem cells, wherein said genetic manipulation introduces a transgene into said embryonic stem cells; and (c) introducing one or more of said embryonic stem cells into said tetraploid blastocyst, thereby generating a transgenic embryo; and (d) implanting said transgenic embryo into a foster mother under conditions favoring development of said embryo into a transgenic mouse.

9. The method of claim 8, wherein said embryonic stem cells are R1 cells.

10. The method of claim 8, wherein said embryonic stem cells are GS1 cells.

11. The method of claim 8, wherein said embryonic stem cells are J1 cells.

12. The method of claim 8, wherein said embryonic stem cells are TT2 cells.

13. The method of claim 8, wherein said embryonic stem cells are introduced into said tetraploid blastocyst by microinjection.

14. The method of claim 8, wherein said embryonic stem cells comprise at least one transgene.

* * * * *